United States Patent [19]
Horn et al.

[11] Patent Number: 5,558,516
[45] Date of Patent: Sep. 24, 1996

[54] PRETREATED PLASTIC DENTAL APPLIANCES AND METHODS

[75] Inventors: Jerold S. Horn, Los Angeles; James F. Forbes, Monrovia, both of Calif.

[73] Assignee: Minnesota Mining and Manufacturing Company, St. Paul, Minn.

[21] Appl. No.: 323,041

[22] Filed: Oct. 14, 1994

[51] Int. Cl.$^6$ ............................................. A61C 7/16
[52] U.S. Cl. ................................. 433/9; 433/228.1
[58] Field of Search ........................ 433/9, 180, 183, 433/226, 228.1

[56] References Cited

U.S. PATENT DOCUMENTS

| | | |
|---|---|---|
| 3,922,787 | 12/1975 | Fischer et al. . |
| 4,363,624 | 12/1982 | Johnston ........................ 433/9 |
| 4,978,007 | 12/1990 | Jacobs et al. ................. 206/469 |
| 5,078,596 | 1/1992 | Carberry et al. ............... 433/8 |
| 5,141,436 | 8/1992 | Orlowski et al. ............. 433/226 |
| 5,172,809 | 12/1992 | Jacobs et al. ................. 206/368 |
| 5,207,577 | 5/1993 | Müller et al. ............ 433/228.1 X |
| 5,221,202 | 6/1993 | James ............................. 433/9 |
| 5,254,002 | 10/1993 | Reher et al. .................... 433/8 |
| 5,277,739 | 1/1994 | Müller et al. ............. 433/180 X |
| 5,295,824 | 3/1994 | Wong ............................. 433/9 |

OTHER PUBLICATIONS

Nitkin et al, "An Improved Technique for the Retention of Polycarbonate Crowns", J. Dent. Child, Mar.–Apr., 1977 pp. 108–110.

Tsamtsouris et al., "An Improved Method to Cement Polycarbonate Crowns on Deciduous Anterior Teeth", Quint. Int., Feb. 1977, vol. 2 pp. 47–50.

BSI PhotoLink Surface Modification Guide, BSI Corp., 1994.

Swanson et al., "Use Photochemistry to Modify Membranes", Chemtech, 1992, pp. 624–626.

Amos et al., "Surface Modification of Polymers by Photochemical Immobilization", The 17th Annual Meeting of the Society for Biomaterials, May 1991.

*Primary Examiner*—Robert P. Swiatek
*Attorney, Agent, or Firm*—Gary L. Griswold; Walter N. Kirn; Dale A. Bjorkman

[57] ABSTRACT

A method for pretreating a plastic dental appliance having a surface to be bonded to a tooth comprising applying a pretreatment composition comprising i) a polymerizable component, ii) a solvent capable of at least partially solubilizing the plastic dental appliance, and iii) a photoinitiator system to the surface of the dental appliance. Components i) and ii) may be the same or different materials. The polymerizable component of the pretreatment composition is then polymerized by exposure to actinic radiation. The present invention also provides pretreated plastic dental appliances prepared by this method. Optionally, the plastic dental appliance may additionally be precoated with an orthodontic adhesive and packaged accordingly.

21 Claims, No Drawings

PRETREATED PLASTIC DENTAL APPLIANCES AND METHODS

FIELD OF THE INVENTION

This invention relates to bonding of dental appliances to substrates. More specifically, this invention relates to bonding of plastic dental appliances to teeth.

BACKGROUND OF THE INVENTION

U.S. Pat. No. 5,141,436 to Orlowski, et. al. discloses a method for bonding a polymeric article to teeth employing a light curable primer. In this method, the surface of a tooth is first etched and a primer is applied to the polymeric article to be bonded to the tooth. The primer comprises light curable acrylate or methacrylate monomers and a volatile solvent which softens or partially dissolves the polymeric material of the article. Polymerization initiators and/or activators are optionally provided in the primer. A light curable adhesive is then applied to the article or the tooth, and the article is placed on the tooth. The primer and the adhesive are then cured by a light induced polymerization reaction.

U.S. Pat. No. 5,295,824 to Wong discloses plastic orthodontic brackets having an adhesive primer layer. A solvating mixture of solvents and acrylic monomers is applied to the bonding surface of a plastic bracket and allowed to attack (solvate) and diffuse into the plastic substrate. The bracket is then heated to volatilize the solvents and lower molecular weight monomers to leave a coating or layer of acrylic material which is predominantly monomeric and is at least partially embedded in the plastic bracket.

SUMMARY OF THE INVENTION

The present invention provides a method for pretreating a plastic dental appliance having a surface to be bonded to a tooth comprising applying a pretreatment composition comprising i) a polymerizable component, ii) a solvent capable of at least partially solubilizing the plastic dental appliance, and iii) a photoinitiator system to the surface of the dental appliance. Components i) and ii) may be the same or different materials. The polymerizable component of the pretreatment composition is then polymerized by exposure to actinic radiation. The present invention also provides pretreated plastic dental appliances prepared by this method. Optionally, the plastic dental appliance may additionally be precoated with an orthodontic adhesive and packaged accordingly.

DETAILED DESCRIPTION

The pretreatment composition of the present invention contains a polymerizable component together with a solvent that is capable of partially solubilizing the plastic dental appliance. The polymerizable component optionally may be selected from any materials suitable for use as dental adhesive resins that will alone or in combination with other materials act to at least partially solubilize the plastic dental appliance. Examples of such materials are acrylates and methacrylates, such as C 1–6 alkyl acrylates and methacrylates, C 1–12 alkoxyalkyl acrylates and methacrylates and C 1–6 alkyl triacrylates and methacrylates, and more preferably C 1–4 alkyl acrylates and methacrylates, C 1–4 alkoxyalkyl acrylates and methacrylates and C 1–6 glycol diacrylates and dimethylacrylates. Other preferred polymerizable components are monomers traditionally used in dental materials, such as the dimethacrylate derived from the reaction between methacrylic acid and the diglycidyl ether of bisphenol A ("Bis-GMA"), tetraethylene glycol dimethacrylate, Bisphenol A diethyleneglycol dimethacrylate ("Bis-EMA") and triethylene glycol dimethacrylate ("TEGDMA"). Polymers, such as polymethyl methacrylate, may also be incorporated in the pretreatment compositions as appropriate.

Particularly preferred pretreatment compositions comprise mixtures of polymerizable components, and particularly incorporate polymerizable components of different molecular weights. For example, preferred pretreatment compositions will comprise one polymerizable component of comparatively low molecular weight, such as methyl methacrylate, and one of higher molecular weight, such as Bis-GMA. For purposes of the present invention, a polymerizable component will be considered to have a low molecular weight if its number average molecular weight is below about 280, and will be considered to have a high molecular weight if its number average molecular weight is above about 400. Preferably, the ratio of low molecular weight polymerizable component to high molecular weight polymerizable component is from about 1:5 to about 3:2 by weight. Optionally, the components of the pretreatment composition may be separately applied. For example, the low molecular weight polymerizable component may be applied to the plastic dental appliance first, followed by application of the high molecular weight polymerizable component. Either or both solutions may contain the photoinitiator.

The pretreatment composition of the present invention may optionally additionally contain a non-polymerizable component, which preferably is any non-polymerizable component that is capable of at least partially solubilizing the plastic dental appliance. Typically, a polymer is solubilized or partially solubilized in a solvent that has a solubility parameter that is close in value to the solubility parameter of the polymer. Preferably, the solubility parameter of the solvent is within one unit of the solubility parameter of the polymer of the plastic dental appliance. More preferably, the solubility parameter of the solvent is within 0.5 units and most preferably within 0.2 units of the solubility parameter of the polymer of the plastic dental appliance. For example, the polymer bisphenol A polycarbonate has a solubility parameter of 9.6 $(cal/cm^3)^{0.5}$. Preferred solvents for this class of polymer have a solubility parameter of between 8.6 and 10.6, and more preferably between 9.1 and 10.1. Examples of suitable solvents include acetone (9.9) methyl acetate (9.6), methyl ethyl ketone (9.3), methyl propyl ketone (8.7), and tetrahydrofuran (9.1) and blends thereof.

The pretreatment composition used in the present invention contains a photoinitiator system. The use of a photoinitiator system provides particular advantage to the pretreatment compositions of the present invention because they provide excellent on-demand control of polymerization. The timing of the polymerization of the pretreatment compositions may be easily and strictly controlled in processing the plastic dental appliance during production. The photoinitiator system should be capable of promoting crosslinking of the polymerizable component. Preferably, the polymerizable component is crosslinked by a free radical mechanism, and more preferably has an ethylenically unsaturated moiety capable of crosslinking reaction on exposure of the photoinitiator to light of a suitable wavelength and intensity. It also preferably is sufficiently shelf stable and free of undesirable coloration to permit its storage and use under typical dental conditions. Visible light photoinitiators are preferred.

The photoinitiator system contains a free radical initiator that acts as a source of free radicals when activated.

Examples of free radical initiators include camphorquinone, benzoin methyl ether, aryliodonium salts, and the like. Certain free radical initiators can be used alone, however, most are most effectively used in combination with one or more accelerators and/or sensitizers (for example, amines, peroxides, phosphorus compounds, ketones and alphadiketone compounds).

Preferred visible light-induced initiator systems include camphorquinone (which typically is combined with a suitable hydrogen donor such as an amine), diaryliodonium simple salts, diaryliodonium metal complex salts, chromophore-substituted halomethyl-s-triazines and halomethyl oxadiazoles. Particularly preferred visible light-induced photoinitiator systems include combinations of an alpha-diketone, e.g., camphorquinone, and a diaryliodonium salt, e.g., diphenyliodonium chloride, bromide, iodide or hexafluorophosphate, with or without additional hydrogen donors (such as sodium benzene sulfinate, amines and amine alcohols).

Preferred ultraviolet light-induced polymerization initiator systems include ketones such as benzyl and benzoin, and acyloins and acyloin ethers. Preferred commercially available ultraviolet light-induced polymerization initiator systems include 2,2-dimethoxy-2-phenylacetophenone ("IRGACURE 651") and benzoin methyl ether (2-methoxy-2-phenylacetophenone), both from Ciba-Geigy Corp.

Typically, the photoinitiator system components will be present at a total weight of about 0.01 to about 5%, more preferably from about 0.1 to about 2 %, based on the total weight of the pretreating composition.

The pretreatment composition is applied to the plastic dental appliance in an amount effective to enhance bonding of the appliance to the intended substrate, when used in conjunction with orthodontic adhesive. In the case of plastic orthodontic brackets, the pretreatment composition is preferably provided as a coating of at least about 0.01 ml/cm$^2$, and more preferably at least about 0.1 ml/cm$^2$. The pretreatment compositions may be applied by a dropper, brush, syringe or other appropriate means.

The plastic dental appliance may be any of the appropriate plastic dental appliances such as those currently available in the orthodontic bracket market. Examples of such plastic brackets include filled and unfilled polycarbonate brackets, such as described in U.S. Pat. No. 3,922,787, U.S. Pat. No. 5,078,596 and U.S. Pat. No. 5,254,002. Other materials from which the plastic dental appliance may be fabricated include the polysulfones, polyacrylonitrile-butadiene-styrene copolymers (ABS polymers), polymethyl methacrylate (PMMA) and the like.

Once pretreated and exposed to actinic radiation, the plastic dental appliance may be packaged for sale to dental professionals for use in the oral environment. Because the pretreatment compositions have been polymerized, no special precautions need be taken with the product in this form to be protected from exposure to actinic radiation.

Plastic dental appliances that have been pretreated in accordance with the present invention may additionally be provided with an adhesive precoat and packaged in a suitable package, such as described for orthodontic brackets in U.S. Pat. Nos. 4,978,007 and 5,172,809, the disclosures of which are hereby incorporated by reference.

It has surprisingly been found that plastic dental appliances that have been pretreated in the manner of the present invention exhibit superior adhesion bond strength to enamel as compared to like plastic dental appliances that have not been pretreated. Preferably, the pretreated plastic dental appliances have an Adhesion Bond Strength that is more than 2 times the Adhesion Bond Strength of a like plastic dental appliance that has not been pretreated. More preferably, the pretreated plastic dental appliances have an Adhesion Bond Strength that is more than 5 times, and most preferably more than 8 times that of the Adhesion Bond Strength of a like plastic dental appliance that has not been pretreated. Adhesion Bond Strengths are determined in the following manner.

Shear-Peel Adhesion Bond Strength

The shear strengths of the brackets reported herein were measured as follows:

The brackets were bonded to grooved metal rings that hold the adhesive mechanically. These cylindrical Type 303 stainless steel rings are 7/8" in diameter and 0.30" high. Each ring has six (6) grooves that have been machined into the outer surface. The grooves are 0.016+/−0.001" wide and 0.014" deep and spaced at 0.009+/−0.001 ". The grooves are partially closed by application of a circular pitch knurling tool (80TPI/189T with 70 degree included tooth angle).

The brackets are bonded by applying 3M Transbond XT Visible Light Cure Primer to the metal ring and 3M Transbond XT Visible Light Cure Adhesive to the bracket that has been pretreated as described above. The bracket with adhesive is then positioned on the grooved ring so that the archwire slot of the bracket is parallel to the grooves of the metal ring. Excess adhesive is removed, and the adhesive is cured by a ten second exposure to a 3M ORTHOLUX XT curing light. After overnight storage at room temperature, the metal ring is mounted on a support fixture in the lower jaws of an Instron Universal Testing Machine so that the plane of the ring is perpendicular to the cross head motion. A stainless steel wire loop (0.018 to 0.020") is placed in the upper jaws of the testing machine. This loop is adjusted so that it fits over the bracket and then contacts the bracket under the tie wings. Load is applied to the bracket at a rate of 0.2"/min. until bond failure. The maximum load is recorded as the bond strength. This procedure is repeated until all brackets have been tested. A standard test sample is five (5) brackets.

The following examples are provided to illustrate the present invention. These examples should not be considered to limit the scope of the present invention. Unless otherwise indicated, all amounts and ratios are by weight.

EXAMPLE 1

Polymethyl methacrylate (2.0 g, Polysciences, Inc., Cat. No. 04554) was added to 8.0 g of methyl methacrylate and stirred. Bis-EMA (10.0 g, Diacryl 101), camphorquinone (0.1 g) and ethyl 4-dimethylaminobenzoate (0.05 g, Aldrich E2, 490-5) were added and stirred till dissolved. The ends of 1/4" diameter polycarbonate cylinders were swabbed with the solution and then covered with a glass microscope slide and cured with an Ortholux XT Curing Light. The samples were separated from the glass plate and pressed together with TRANSBOND XT Visible Light Cure Adhesive (3M Unitek) to form an 0.008" thickness of adhesive which was cured with a 60 second exposure to light from the Ortholux XT Curing Light. The cylinders average (standard deviation) bond stress was 960 (426) psi as compared to no treatment of the cylinders at 61 (35) psi.

EXAMPLE 2

Polymethyl methacrylate (2.0 g, Polysciences, Inc., Cat. No. 04554) was added to 2-ethoxy-2-ethoxyethyl methacrylate (8.0 g, Esschem X843000?) and stirred. Bisphenol A diethyleneglycol dimethacrylate (10.0 g, Diacryl 101), camphorquinone (0.1 g) and ethyl 4-dimethylaminobenzoate (0.05 g, Aldrich E2, 490-5) were added and stirred until dissolved. The ends of ¼" diameter polycarbonate cylinders were treated and adhesively bonded as in Example 1. The cylinders average (standard deviation) bond stress was 1290 (535) psi.

EXAMPLE 3

A cotton swab saturated with methyl methacrylate was rubbed across the base of a Tella-Tech Lower Anterior Plastic Bracket (polycarbonate, #124R) and allowed to stand for 60 seconds. TRANSBOND Adhesion Primer (1 drop, p/n 704-059, bisphenol A diglycidal dimethacrylate (49.5%), triethylene glycol (49.5%) dimethacrylate, 4-dimethylaminophenethyl alcohol, (<1) camphorquinone (<1%) and triphenylantimony (<1%)) was placed on the base and cured for 20 seconds with the Ortholux Curing Light. The brackets were then stored in air and intermittent fluorescent light for 6 days and tested for shear-peel bond strength with TRANSBOND XT Visible Light Cure Adhesive (3M Unitek) per the Shear-Peel Adhesion Bond Strength procedure above. The average (standard deviation) bond strength was 13 (4) lbs./bracket as compared to treatment of the brackets per the bracket manufacturer's with Spirit No-Mix Primer (ORMCO Co., p/n 740-0077) at 4 (2) lbs. /bracket.

EXAMPLE 4

Equal parts by weight of methyl methacrylate ("MMA") and TRANSBOND Adhesion Primer (p/n 704–059) were mixed until homogenous. The base of a Tella-Tech Lower Anterior Plastic Bracket (polycarbonate, #124R) was covered with the solution, allowed to stand for 60 seconds and cured for 20 seconds with the Ortholux Curing Light. The brackets were then stored in air and intermittent fluorescent light for 6 days and tested for shear-peel bond strength per Example 3. The average (standard deviation) bond strength was 23 (4) lbs./bracket.

EXAMPLE 5

Methyl methacrylate and TRANSBOND Adhesion Primer were mixed and RMO Siamese Plastic Brackets (polycarbonate) were coated and bonded as in Example 4.

| MMA | Transbond XT | Average, lbs/bkt | Standard Deviation, lbs/bkt |
|---|---|---|---|
| 100% | 0% | 16 | 5.4 |
| 80% | 20% | 29 | 9.9 |
| 60% | 40% | 28 | 7.8 |
| 40% | 60% | 40 | 13.6 |
| 20% | 80% | 40 | 11.1 |
| 0% | 100% | 17 | 4.7 |

This example demonstrates that the ratio of high molecular weight polymerizable component to low molecular weight polymerizable component has an effect on the observed adhesive bond strength.

EXAMPLE 6

Acetone and TRANSBOND Adhesion Primer were mixed and RMO Lower Anterior Plastic Brackets (polycarbonate) were coated and bonded as in Example 4.

| Acetone | Transbond XT | Average, lbs/bkt | Standard Deviation, lbs/bkt |
|---|---|---|---|
| 80% | 20% | 38 | 8.4 |
| 60% | 40% | 42 | 7.8 |
| 40% | 60% | 51 | 11.7 |
| 20% | 80% | 37 | 11.2 |
| 0% | 100% | 17 | 4.7 |

This example demonstrates the effect of incorporating a non-polymerizable component together with a polymerizable component in pretreatment compositions of the present invention.

EXAMPLE 7

BisEMA (Diacryl 101) and MMA with light cure additives (0.25% CPQ and 1.0% EDMAB) were mixed and Forestadent Ceramic Filled Plastic Brackets (polycarbonate) were coated and bonded as in Example 4.

| BisEMA | MMA | Average, lbs/bkt | Standard Deviation, lbs/bkt |
|---|---|---|---|
| 100% | 0% | 5 | 0.6 |
| 67% | 33% | 30 | 4.9 |
| 33% | 67% | 37 | 1.8 |

This example demonstrates that the ratio of high molecular weight polymerizable component to low molecular weight polymerizable component has an effect on the observed adhesive bond strength.

EXAMPLE 8

MMA and Acetone with light cure additives (0.05% CPQ and 0.2% EDMAB) were mixed and RMO Wide Plastic Brackets (polycarbonate) were coated and bonded as in Example 4.

| MMA | Acetone | Average, lbs/bkt | Standard Deviation, lbs/bkt |
|---|---|---|---|
| 80% | 20% | 13 | 2.5 |
| 60% | 40% | 9 | 1.2 |
| 40% | 60% | 21 | 3.9 |
| 20% | 80% | 26 | 10.1 |

This example demonstrates the effect of incorporating a non-polymerizable component together with a polymerizable component in pretreatment compositions of the present invention.

EXAMPLE 9

TEGDMA with light cure additives (0.25% CPQ and 1.0% EDMAB) were mixed and Forestadent Ceramic Filled Plastic Brackets (polycarbonate) were coated and bonded as in Example 4. The average (standard deviation) bond strength was 27 (1.6) lbs/bracket.

EXAMPLE 10

MMA and TRANSBOND Adhesion Primer at the indicated ratios were coated on Tella-Tech Lower Anterior brackets and cured at the indicated times after application to the bracket. The brackets were then stored in air and intermittent fluorescent light for 3 days and tested for shear-peel bond strength.

| % MMA/<br>% TRANSBOND XT | Time,<br>Seconds | Average,<br>lbs/bkt | Standard Deviation,<br>lbs/bkt |
| --- | --- | --- | --- |
| 40%/60% | 10 | 11 | 4.4 |
| 20%/80% | 32 | 24 | 2.9 |
| 20%/80% | 316 | 23 | 3.4 |
| 40%/60% | 1000 | 25 | 3.9 |
| 60%/40% | 316 | 21 | 2.1 |
| 60%/40% | 32 | 22 | 3.8 |
| 40%/60% | 100 | 21 | 1.6 |
| 40%/60% | 100 | 22 | 3.3 |
| 40%/60% | 100 | 18 | 2.5 |
| 40%/60% | 100 | 24 | 1.6 |

Regression analysis of the bond strength indicated that the bond strength stopped increasing after 1 minute and may start to decrease if cure was delayed to after 15 minutes after application to the bracket. In addition, the higher concentration of TRANSBOND XT primer increased the bond strength as a result of triethylene glycol dimethacrylate in the primer, which is also a solvent for the plastic.

EXAMPLE 11

TEGDMA with light cure additives (0.25% CPQ and 1.0% EDMAB) was coated on Tella-Tech Lower Anterior brackets and cured at the indicated times after cure. The brackets were then stored in air and intermittent fluorescent light for 3 days and tested for shear-peel bond strength.

| Time | Average,<br>lbs/bkt | Standard Deviation,<br>lbs/bkt |
| --- | --- | --- |
| 1 min. | 19 | 4.3 |
| 1 hr. | 21 | 3.2 |
| 6 hrs. | 20 | 2.2 |

The results show that TEGDMA is an effective polymerizable component for the pretreatment composition of the present invention.

EXAMPLE 12

40% MMA/60% TRANSBOND XT primer were mixed and IGLOO Plastic Brackets (polysulfone) were coated and bonded as in Example 4. The average (standard deviation) bond strength was 20 (2.3) lbs/bracket as compared to 8 (3.8) lbs/bracket for the uncoated brackets. This result shows that this technique is applicable to plastics other than polycarbonate.

EXAMPLE 13

40% MMA/60% TRANSBOND XT primer were mixed and Tella-Tech Lower Anterior brackets (polycarbonate) were coated and bonded with the following adhesives as in Example 4.

| Adhesive | Average,<br>lbs/bkt | Standard Deviation,<br>lbs/bkt |
| --- | --- | --- |
| Unite | 21 | 5.5 |
| Insta-Bond | 18 | 6.6 |
| Rely-a-Bond | 14 | 2.8 |
| System 1+ | 15 | 2.4 |
| Concise | 11 | 3.2 |
| Phase II | 14 | 1.9 |
| Transbond XT | 20 | 3.5 |
| Light Bond | 21 | 3.9 |
| Mono-Lok 2 | 10 | 1.5 |
| Sequence | 12 | 4.0 |
| Ultralight | 17 | 3.1 |

This experiment demonstrates that Brackets that have been pretreated with a pretreatment composition as described herein provide excellent bond strengths when the brackets are adhered to tooth surfaces with many types of orthodontic adhesives.

EXAMPLE 14

A pretreatment composition was prepared by mixing three (3) parts of MMA and one (1) part of Bis-GMA together until homogenous. 0.375% camphorquinone (CPQ) and 1% ethyl-4-dimethyl-amino benzoate (EDMAB) were dissolved in the resin mixture. The bonding base of plastic brackets (20% glass filled polycarbonate, LNP DF1004) were prepared by application of approximately 2.5 microliters of solution. The brackets were allowed to dry of 2–3 minutes and then cured by exposure to an ORTHOLUX XT curing light for 10 seconds. The brackets were stored in air and intermittent exposure to fluorescent light and then tested for shear/peel bond strength using the procedure of Example 4 with the following adhesives.

| Adhesive | # of Brackets | Bond Strength lbs/bkt | |
| --- | --- | --- | --- |
| | | Average | S.D. |
| Concise Orthodontic bonding adhesive | 15 | 37 | 6.6 |
| Transbond XT Adhesive | 15 | 30 | 8.3 |

What is claimed:

1. A method for pretreating a plastic dental appliance having a surface to be bonded to a tooth comprising
   a) applying a pretreatment composition comprising
      i) a polymerizable component,
      ii) a solvent capable of at least partially solubilizing the plastic dental appliance, and
      iii) a photoinitiator system,
      wherein i) and ii) may be the same or different materials, to the surface of the dental appliance; and
   b) before application of an orthodontic adhesive to said surface, exposing said applied pretreatment composition to actinic radiation in an amount sufficient to polymerize said polymerizable component.

2. The method of claim 1, wherein the polymerizable component is selected from the group consisting of acrylates and methacrylates.

3. The method of claim 1, wherein the polymerizable component comprises at least one monomer selected from the group consisting of C 1–6 alkyl acrylates, C 1–6 alkyl methacrylates, C 1–12 alkoxyalkyl acrylates and C 1–12 alkoxyalkyl methacrylates.

4. The method of claim 1, wherein the polymerizable component comprises at least one monomer selected from the group consisting of C 1–4 alkyl acrylates, C 1–4 alkyl methacrylates, C 1–4 alkoxyalkyl acrylates and C 1–4 alkoxyalkyl methacrylates.

5. The method of claim 1, wherein the polymerizable component comprises a monomer selected from the group consisting of Bis-GMA, Bis-EMA and TEGDMA.

6. The method of claim 1, wherein the pretreatment composition comprises a mixture of polymerizable components, wherein at least one of said polymerizable components is a solvent that is an acrylate or methacrylate having a molecular weight below about 280, and at least one of said polymerizable components has a number average molecular weight above about 400.

7. The method of claim 6, wherein the weight ratio of low molecular weight polymerizable component to high molecular weight polymerizable component is from about 1:5 to about 3:2.

8. The method of claim 6, wherein the low molecular weight polymerizable component is applied to the plastic dental appliance in a separate first application, followed by a separate second application of the high molecular weight polymerizable component.

9. The method of claim 1, wherein the solvent capable of at least partially solubilizing the plastic dental appliance is a non-polymerizable solvent.

10. The method of claim 9, wherein the non-polymerizable solvent is selected from the group consisting of acetone, methyl acetate, methyl ethyl ketone, methyl propyl ketone, and tetrahydrofuran and blends thereof.

11. The method of claim 1, wherein the plastic dental appliance is an orthodontic bracket.

12. The method of claim 1, wherein the plastic dental appliance is made from polycarbonate.

13. A pretreated dental appliance made by the process of claim 1.

14. A method for providing a pre-coated plastic dental appliance having a surface to be bonded to a tooth comprising, in order, a) applying a pretreatment composition comprising
  i) a polymerizable component,
  ii) a solvent capable of at least partially solubilizing the plastic dental appliance, and
  iii) a photoinitiator system,
  wherein i) and ii) may be the same or different materials, to the surface of the dental appliance;
 b) exposing said applied pretreatment composition to actinic radiation in an amount sufficient to polymerize said polymerizable component;
 c) applying a predetermined amount of an orthodontic adhesive to the surface of the dental appliance; and
 d) packaging the adhesive-coated dental appliance in a package that is resistant to transmission of actinic radiation.

15. The method of claim 14, wherein the polymerizable component comprises at least one C 1–4 or alkoxy alkyl acrylate or methacrylate.

16. The method of claim 14 wherein the polymerizable component comprises monomer selected from the group consisting of Bis-GMA, Bis-EMA and TEGDMA.

17. The method of claim 14, wherein the pretreatment composition comprises a mixture of polymerizable components, wherein at least one of said polymerizable components is a solvent that is an acrylate or methacrylate having a molecular weight below about 280, and at least one of said polymerizable components has a number average molecular weight above about 400.

18. The method of claim 17, wherein the weight ratio of low molecular weight polymerizable component to high molecular weight polymerizable component is from about 1:5 to about 3:2.

19. The method of claim 14, wherein the plastic dental appliance is an orthodontic bracket.

20. The method of claim 14, wherein the plastic dental appliance is made from polycarbonate.

21. A pretreated dental appliance made by the process of claim 14.

* * * * *